(12) United States Patent
Phadke et al.

(10) Patent No.: US 9,006,423 B2
(45) Date of Patent: Apr. 14, 2015

(54) PROCESS FOR MAKING A 4-AMINO-4-OXOBUTANOYL PEPTIDE CYCLIC ANALOGUE, AN INHIBITOR OF VIRAL REPLICATION, AND INTERMEDIATES THEREOF

(71) Applicant: Achillion Pharmaceuticals, Inc., New Haven, CT (US)

(72) Inventors: Avinash Phadke, Branford, CT (US); Akihiro Hashimoto, Branford, CT (US)

(73) Assignee: Achillion Pharmaceuticals Inc., New Haven, CT (US)

( * ) Notice: Subject to any disclaimer, the term of this patent is extended or adjusted under 35 U.S.C. 154(b) by 0 days.

(21) Appl. No.: 14/215,528

(22) Filed: Mar. 17, 2014

(65) Prior Publication Data

US 2014/0275520 A1 Sep. 18, 2014

Related U.S. Application Data

(60) Provisional application No. 61/789,340, filed on Mar. 15, 2013.

(51) Int. Cl.
| | |
|---|---|
| C07D 417/14 | (2006.01) |
| C07D 403/12 | (2006.01) |
| C07D 403/14 | (2006.01) |
| C07K 5/078 | (2006.01) |
| C07C 51/347 | (2006.01) |
| A61K 38/05 | (2006.01) |

(52) U.S. Cl.
CPC ........... *C07K 5/06165* (2013.01); *C07C 51/347* (2013.01); *A61K 38/05* (2013.01)

(58) Field of Classification Search
USPC .......................................... 540/460; 546/153
See application file for complete search history.

(56) References Cited

U.S. PATENT DOCUMENTS

| | | | |
|---|---|---|---|
| 6,867,185 B2 | 3/2005 | Campbell et al. | |
| 6,872,805 B2 | 3/2005 | Campbell et al. | |
| 6,908,901 B2 | 6/2005 | Bailey et al. | |
| 6,995,174 B2 | 2/2006 | Wang et al. | |
| 7,041,698 B2 | 5/2006 | Ripka et al. | |
| 7,176,208 B2 | 2/2007 | Nakajima et al. | |
| 7,906,619 B2 | 3/2011 | Phadke et al. | |
| 8,614,180 B2 * | 12/2013 | Phadke et al. ................. | 514/4.3 |
| 2003/0224977 A1 | 12/2003 | Llinas-Brunet et al. | |
| 2004/0002448 A1 | 1/2004 | Tsantrizos et al. | |
| 2004/0048802 A1 | 3/2004 | Ripka et al. | |
| 2004/0077551 A1 | 4/2004 | Campbell et al. | |
| 2004/0106559 A1 | 6/2004 | Wang et al. | |
| 2004/0180815 A1 | 9/2004 | Nakajima et al. | |
| 2004/0224900 A1 | 11/2004 | Bailey et al. | |
| 2005/0153877 A1 | 7/2005 | Miao et al. | |
| 2006/0019905 A1 | 1/2006 | Bailey et al. | |
| 2006/0046965 A1 | 3/2006 | Bailey et al. | |
| 2006/0046983 A1 | 3/2006 | Hudyma et al. | |
| 2006/0199773 A1 | 9/2006 | Sausker et al. | |
| 2007/0010455 A1 | 1/2007 | Hewawasam et al. | |
| 2007/0093414 A1 | 4/2007 | Carini et al. | |
| 2007/0099825 A1 | 5/2007 | D'Andrea et al. | |
| 2009/0048297 A1 | 2/2009 | Phadke et al. | |
| 2010/0216725 A1 | 8/2010 | Phadke et al. | |
| 2011/0306771 A1 | 12/2011 | Thompson et al. | |

FOREIGN PATENT DOCUMENTS

| | | |
|---|---|---|
| WO | 9101327 A1 | 2/1991 |
| WO | 0059929 A1 | 10/2000 |
| WO | 02060926 A2 | 8/2002 |
| WO | 03099274 A1 | 12/2003 |
| WO | 03099316 A1 | 12/2003 |
| WO | 2004043339 A2 | 5/2004 |
| WO | 2004072243 A2 | 8/2004 |

(Continued)

OTHER PUBLICATIONS

Andrews et al., "Pyrrodlidine-5,5-trans-lactams. 2. The Use of X-ray Crystal Structure Data in the Optimization of P3 and P4 Substituents" Organic Letters, vol. 4, No. 25, (2002), pp. 4479-4482.

Arasappan, et al., "Hepatitis C Virus NS3-4A serine protease inhibitors: SAR of P2 moiety with improved potency," Bioorganic & Medicinal Chemistry Letters, 15: 4180-4184 (2005).

Barbato, et al., "Inhibitor binding induces active site stabilization of the HCV NS3 protein serine protease domain," The EMBO Journal, 19(6): 1195-1206 (2000).

Chan, T. H. et al. Chemistry of 1,3,5-Tris(trimethylsiloxy)-1-methoxyhexa-1,3,5-triene, a B-Tricarbonyl Trianion Equivalent, Journal of Organic Chemistry, vol. 51, No1. 13, 1986, pp. 2423-2428.

Chan, Weng C., et al., "Basic procedures", FMOC-Solid Phase Peptide Synthesis—A Practical Approach, Oxford University Press, GB, Mar. 2000, pp. 40-76.

Di Marco, et al., "Inhibition of the Hepatitis C Virus NS3/4A Protease," The Journal of Biological Chemistry, 275(10): 7152-7157 (2000).

(Continued)

*Primary Examiner* — Bruck Kifle
(74) *Attorney, Agent, or Firm* — Cantor Colburn LLP

(57) ABSTRACT

The invention provides a process of preparing 4-amino-4-oxobutanoyl peptides and cyclic analogues thereof of Compound I (Compound I)

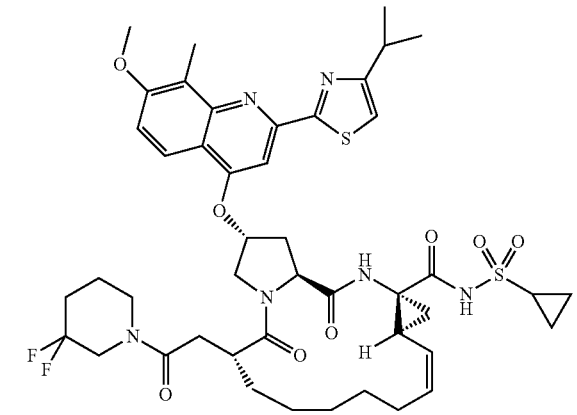

and pharmaceutically acceptable salts thereof.

14 Claims, 1 Drawing Sheet

(56) References Cited

FOREIGN PATENT DOCUMENTS

| WO | 2004094452 A2 | 11/2004 |
| WO | 2004103996 A1 | 12/2004 |
| WO | 2004113365 A2 | 12/2004 |
| WO | 2005007681 A2 | 1/2005 |
| WO | 2005028501 A1 | 3/2005 |
| WO | 2005037214 A2 | 4/2005 |
| WO | 2005046712 A2 | 5/2005 |
| WO | 2005051410 A1 | 6/2005 |
| WO | 2005054430 A2 | 6/2005 |
| WO | 2005070955 A1 | 8/2005 |
| WO | 2005073216 A1 | 8/2005 |
| WO | 2005090383 A2 | 9/2005 |
| WO | 2005095403 A2 | 10/2005 |
| WO | 2006007700 A1 | 1/2006 |
| WO | 2006007708 A1 | 1/2006 |
| WO | 2006020276 A2 | 2/2006 |
| WO | 2006033878 A1 | 3/2006 |
| WO | 2006086381 A2 | 8/2006 |
| WO | 2006096652 A2 | 9/2006 |
| WO | 2007005838 A1 | 1/2007 |
| WO | 2007009109 A2 | 1/2007 |
| WO | 2007009227 A1 | 1/2007 |
| WO | 2007014919 A1 | 2/2007 |
| WO | 2007014927 A3 | 2/2007 |
| WO | 2007015824 A2 | 2/2007 |
| WO | 2007030656 A1 | 3/2007 |
| WO | 2007044893 A2 | 4/2007 |
| WO | 2008086161 A1 | 7/2008 |
| WO | 2010068761 A2 | 1/2010 |

OTHER PUBLICATIONS

Evans, David A., "A General Method for the Synthesis of Enantiomerically Pure B-Substituted, B-Amino Acids through a-Substituted Succinic Acid Derivatives", Journal Organic Chemistry, 1999, 64, pp. 6411-6417.

Goudreau, Nathalie et al. "Potent Inhibitors of the Hepatitis C Virus NS3 Protease: Design and Synthesis of Macrocyclic Substrate-Based B-Strand Mimics", Journal Organic Chemistry, 2004, 69, pp. 6185-6201.

International Search Reprot of the International Searching Authority for International Patent Application No. PCT/US2014/030293; International Filing Date: Mar. 17, 2014; Date of Mailing: May 16, 2014; 5 Pages.

Llinas Brunet, et al., "A Systematic Approach to the Optimization of Substrate-Based Inhibitors of the Hepatitis C Virus NS3 Protease: Discovery of Potent and Specific Tipeptide Inhibitors," J. Med. Chem., 47: 6584-6594, (2004).

Ontoria, et al., "The Design and Enzyme-Bound Crystal Structure of Indoline Based Peptidomimetic Inhibitors of Hepatitis C Virus NS3 Protease," J. Med. Chem. 47: 6443-6446 (2004).

Rakic, et al., "A Small-Molecule Probe for Hepatitis C Virus Replication that Blocks Protein Folding," Chemistry & Biology, 13: 1051-1060 (2006).

Slater, et al., "Pyrrolidine-5,5-trans-lactams. 4. Incorporation of a P3/P4 Urea Leads to Potent Intracellular Inhibitors of Hepatitis C Virus NS3/4A Protease," Organic Letters, 5(24): 4627-4630 (2003).

Tsantrizos, et al., "Macrocyclic Inhibitors of the NS3 Protease as Potential Therapeutic Agents of Hepatitis C Virus Infection," Agnew. Chem. Int. Ed., 42(12): 1355-1360 (2003).

Venkatraman, et al., Discovery of (1R,5S)-N-[3-Amino-1-(cyclobutylmethyl)-2,3-dioxopropyl]-3-[2(S)-[[[(1,1-dimethyl-lethy)aminoicarbonyl] amino]-3,3-dimethyl-1-oxobutyl]-6,6-dimethyl-3-azabicyclo[3.1.0]hexan-2(S)-carboxamide, (J. Med. Chem. (2006), 49, 6074-6086).

Written Opinion for International Application No. PCT/US2009/067507 dated Aug. 24, 2010.

* cited by examiner

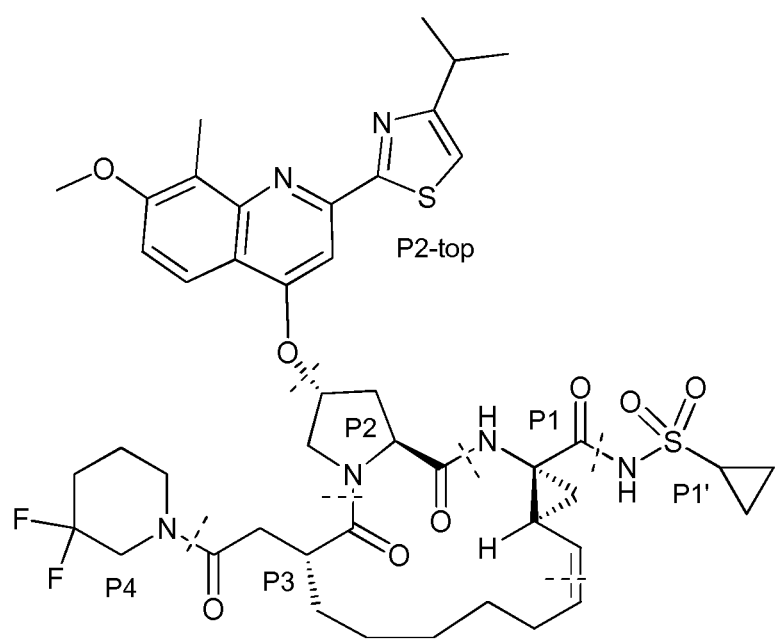

PROCESS FOR MAKING A 4-AMINO-4-OXOBUTANOYL PEPTIDE CYCLIC ANALOGUE, AN INHIBITOR OF VIRAL REPLICATION, AND INTERMEDIATES THEREOF

CROSS REFERENCE TO RELATED APPLICATION

This application claims priority from U.S. Provisional Application No. 61/789,340, filed Mar. 15, 2013, which is hereby incorporated by reference in its entirety.

FIELD OF THE DISCLOSURE

The present invention is directed to a process of preparing a 4-amino-4-oxobutanoyl peptide cyclic compound useful as an antiviral agent. The compound is a potent and/or selective inhibitor of viral replication, particularly Hepatitis C viral replication.

BACKGROUND

An estimated 3% of the world's population is infected with the hepatitis C virus (HCV). Of those exposed to HCV, 80% to 85% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will spontaneously clear HCV.

WO 2010/068761 A2 by Phadke et al. discloses 4-amino-4-oxobutanoyl peptide cyclic analogues, inhibitors of viral replication, which compounds are potent and/or selective inhibitors of Hepatitis C virus replication. Phadke et al. also provides pharmaceutical compositions containing one or more of such compounds, including a salt, solvate, or acylated prodrug of such compounds, and one or more pharmaceutically acceptable carriers.

The present invention provides a novel and improved process for the preparation of Compound 128 disclosed in WO 2010/068761 A2. This process provides certain advantages which are described herein.

SUMMARY

The invention provides a process of preparing a Compound I or its pharmaceutically acceptable salt, represented by the following structure.

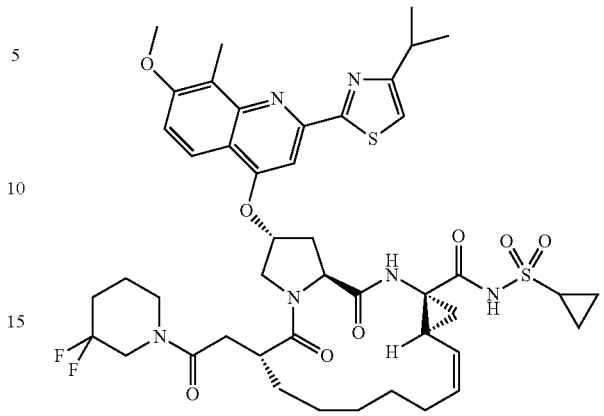

This compound and its pharmaceutically acceptable salt forms, identified as 2R,6R,14aR,16aS,Z)-N-(cyclopropylsulfonyl)-6-(2-(3,3-difluoropiperidin-1-yl)-2-oxoethyl)-2-(2-(4-isopropylthiazol-2-yl)-7-methoxy-8-methylquinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide, will be referred to herein as Compound I herein and its sodium salt form is referred to as Compound IA. This Compound I and its salt forms possess antiviral activity, as disclosed in US2010-0152103.

The invention further comprises novel intermediate compounds useful in making Compound I, and methods of preparing such intermediate compounds.

Thus in a first aspect the invention includes a method of preparing Compound I (or its pharmaceutically acceptable salt) having the following structure:

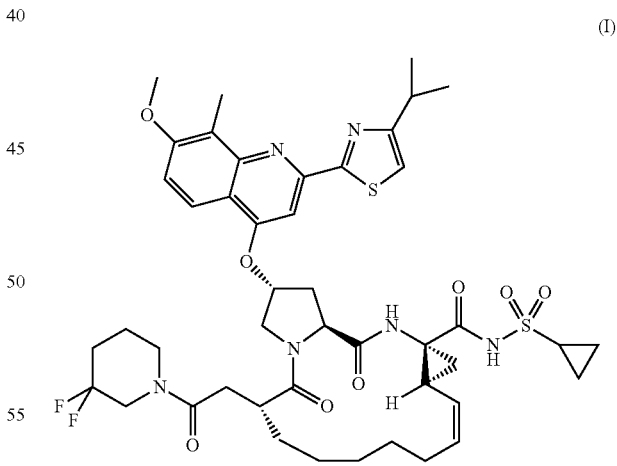

Within Compound I, the hydrogen in the NH group of the sulfonamide group can be replaced by a sodium ion or other pharmaceutically acceptable cationic species.

BRIEF DESCRIPTION OF THE DRAWING

FIG. 1. Amino acids residues P1', P1, P2, P2 Top, P3, and P4 as present in ACH-0142864.

DETAILED DESCRIPTION OF THE INVENTION

Chemical Description and Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well as hydrates of the compound and all pharmaceutically acceptable salts of the compound.

The terms "a" and "an" do not denote a limitation of quantity, but rather denote the presence of at least one of the referenced items. The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless consistent with the methods used to obtain them.

A dash ("—") that is not between two letters or symbols is used to indicate a point of attachment for a substituent. For example, —$(CH_2)C_3$—$C_8$cycloalkyl is attached through carbon of the methylene ($CH_2$) group.

A bond represented by a combination of a solid and dashed line, i.e. ⚌, may be either a single or double bond.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

Chemical Description

The following applications are incorporated by reference for their teachings regarding synthesis of 4-Amino-4-oxobutanoyl macrocyclic peptide analogues: U.S. Provisional Application No. 61/121,378 filed Dec. 10, 2008, U.S. Provisional Application No. 61/226,323 filed Jul. 17, 2009, and U.S. application Ser. No. 12/635,049 filed Dec. 10, 2009. In a number of steps peptide coupling agents are used. A particular peptide coupling agent, such as TBTU may be given as effective for a step in which a peptide coupling agent is used. However in steps in which a peptide coupling agent is used the peptide coupling agent may be N,N,N',N'-tetramethyl-O-(benzotriazol-1-yl)uronium tetrafluoroborate (TBTU), [Bis (dimethylamino)methylene]-1H-1,2,3-triazolo[4,5-b]pyridinium 3-oxide hexafluorophosphate (HATU), benzotriazol-1-yl-oxytripyrrolidinophosphonium hexafluorophosphate (PyBOP), N,N'-Dicyclohexylcarbodiimide (DCC), 1-Ethyl-3-(3-dimethylaminopropyl)carbodiimide (EDC), or a pyridinium coupling agent such as 2-Chloro-1-methylpyridinium iodide (Mukaiyama's reagent) or any other peptide coupling agent recognized in the art.

In certain embodiments it is preferred that the peptide coupling agent is N,N,N',N'-tetramethyl-O-(benzotriazol-1-yl)uronium tetrafluoroborate (TBTU).

The Compound I and salts thereof can be made by reacting Intermediate Compounds A, B and C, as described below, in a suitable reaction scheme.

Intermediate Compound A can be made according to the following Reaction Scheme A.

Reaction Scheme A

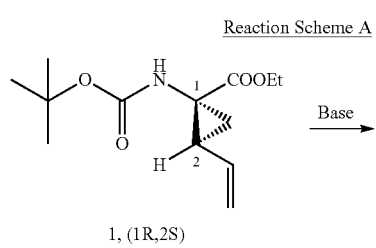

1, (1R,2S)

Base →

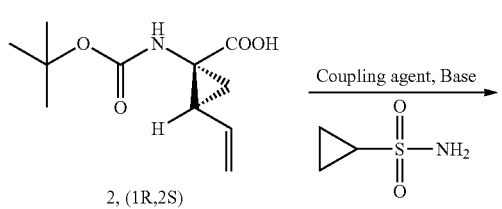

2, (1R,2S)

Coupling agent, Base →

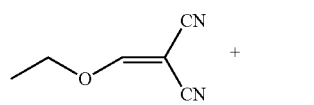
3

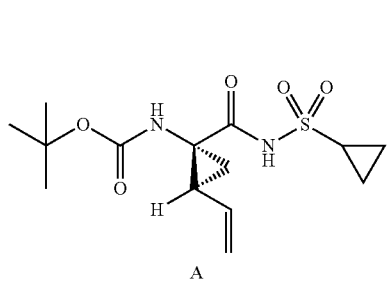

A

Reaction Scheme A is reported in WO2006122188 A2 on page 33, Scheme III, in which the details of the procedure are disclosed on pages 76-78, Steps 1 to 3.

The Intermediate Compound B can be made according to the following Reaction Scheme B:

Reaction Scheme B

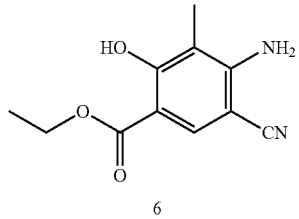

Ethoxymethyl malononitrile
4

+

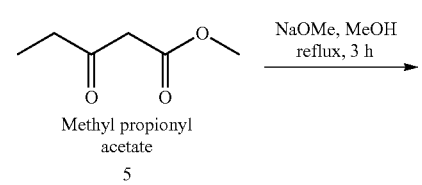

Methyl propionyl acetate
5

NaOMe, MeOH reflux, 3 h →

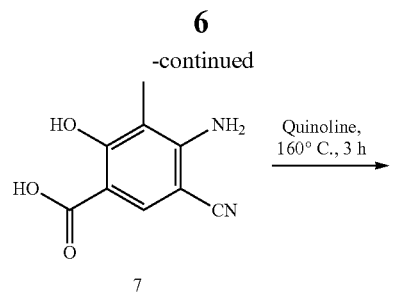
7

Quinoline, 160° C., 3 h →

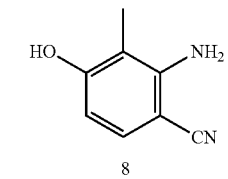
8

MeI, K$_2$CO$_3$, DMF, RT →

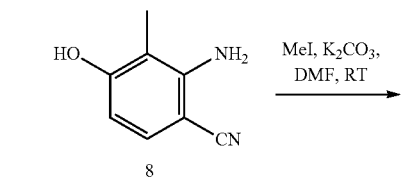
9

MeMgBr, diethyl ether 55° C. →

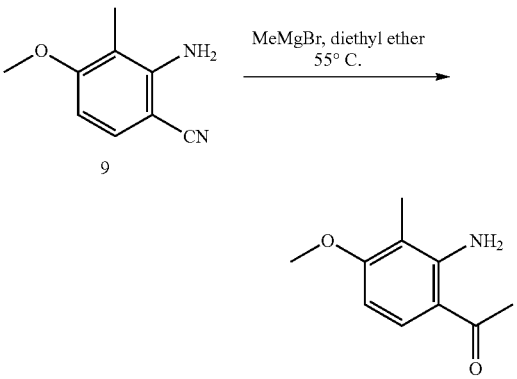
10

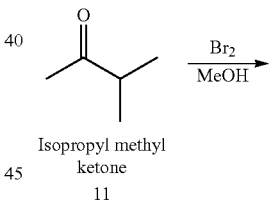

Isopropyl methyl ketone
11

Br$_2$/MeOH →

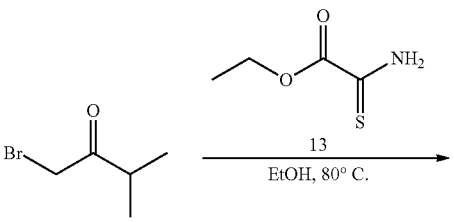
12

Ethyl thioxamate

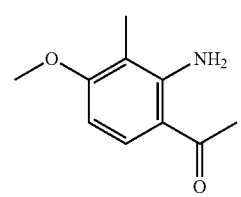
13

EtOH, 80° C. →

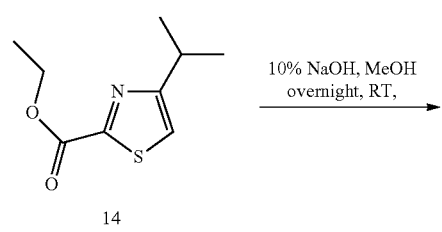
14

10% NaOH, MeOH overnight, RT, →

LiOH, MeOH/water reflux, 3 h →
6

7
-continued

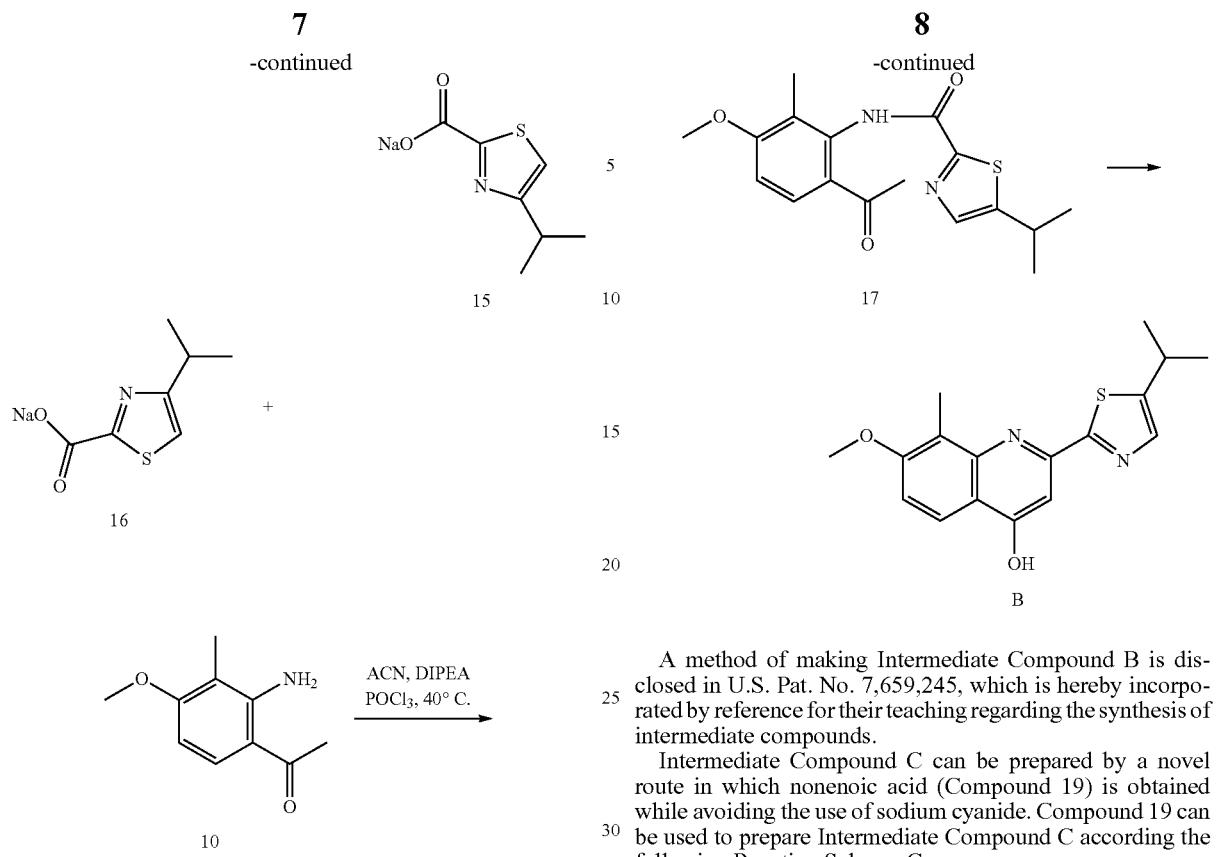

8
-continued

A method of making Intermediate Compound B is disclosed in U.S. Pat. No. 7,659,245, which is hereby incorporated by reference for their teaching regarding the synthesis of intermediate compounds.

Intermediate Compound C can be prepared by a novel route in which nonenoic acid (Compound 19) is obtained while avoiding the use of sodium cyanide. Compound 19 can be used to prepare Intermediate Compound C according the following Reaction Scheme C.

Reaction Scheme C

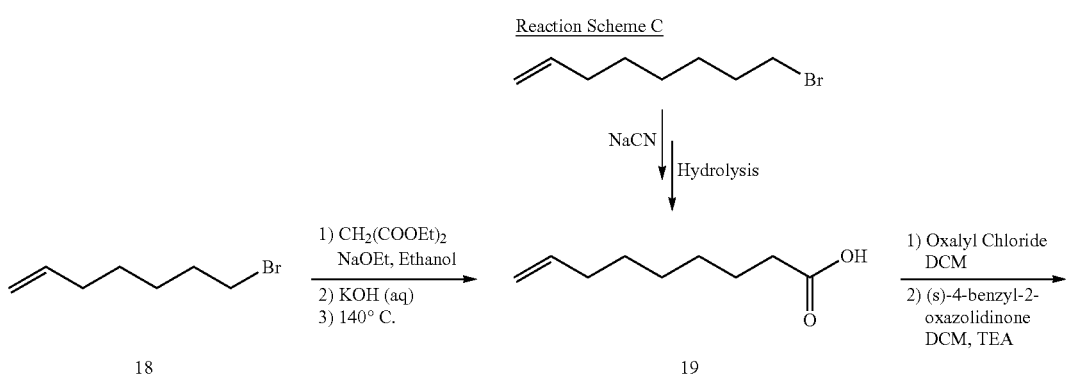

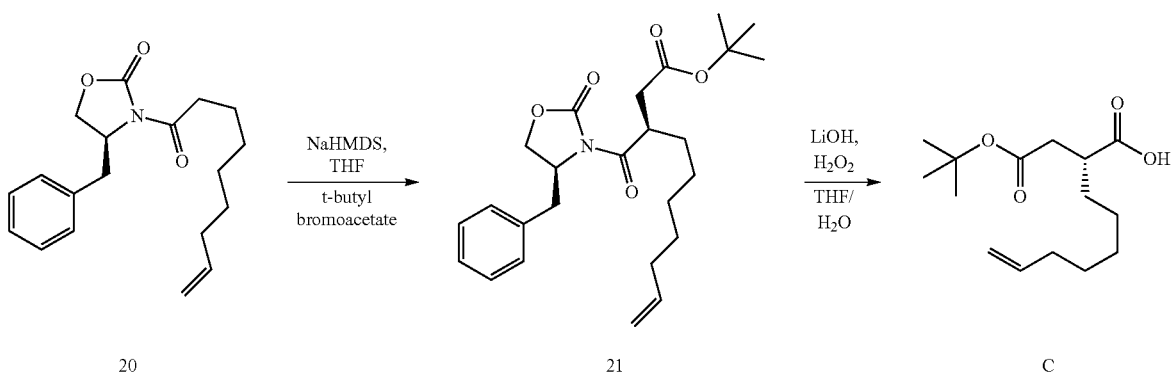

This reaction scheme is particularly advantageous because it avoids the need for reacting sodium cyanide with 1-bromooct-7-ene followed by hydrolysis following, as disclosed by Chan, T. H. and Stossel, D. Journal of Organic Chemistry, 51(13), 2423-8; 1986). In contrast, in the present process an ethoxide salt (sodium ethoxide) is added to a solution of diethylmalonate in solvent such as ethanol. Alternatively this can be performed by adding a strong base such as sodium hydride to a solution of diethylmalonate or other malonate diesters in a polar aprotic solvent such as THF or DMF. To this solution can be added 1-bromo-hept-6-ene. The reaction mixture can be concentrated and then treated with aqueous potassium hydroxide, then acidified and subsequently heated at an elevated temperature, for example, 140° C. to ensure decarboxylation and thereby obtain nonenoic acid. This reaction can generally be represented by the following:

Reaction Scheme C-1

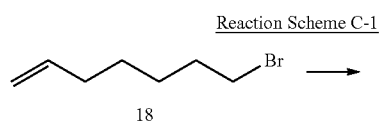

18

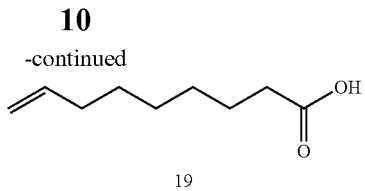

19

The procedure of converting nonenoic acid to Compound C is based on the procedures described in Evans et. al. *J. Org. Chem.* 1999, 64, 6411-6417 (Compound 5b). Thus, Compound 19 can be subsequently reacted with oxalyl chloride or thionyl chloride and then the chiral auxiliary (s)-4-benzyl-2-oxazolidinone to provide Compound 20. Compound 20 can be treated with a strong base such as NaHMDS, LDA, or n-BuLi and then reacted with t-butyl bromoacetate to obtain Compound 21. Compound 21 can be reacted with lithium hydroxide and hydrogen peroxide to remove the 4-benzyl-oxazolidinone and provide Compound C.

After obtaining Intermediate Compounds A, B, and C as described above, novel Compound 30 can be obtained as shown below according to Reaction Scheme D.

Reaction Scheme D

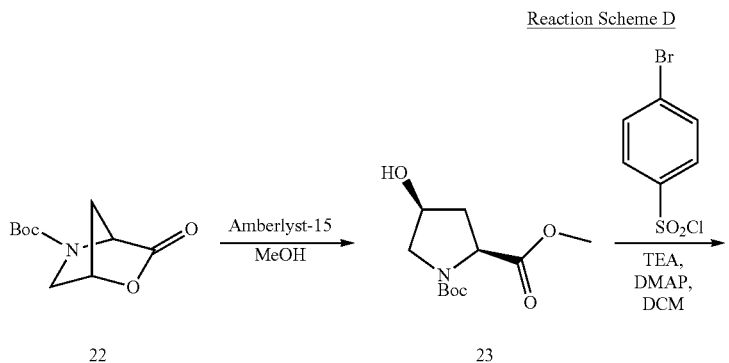

22    23

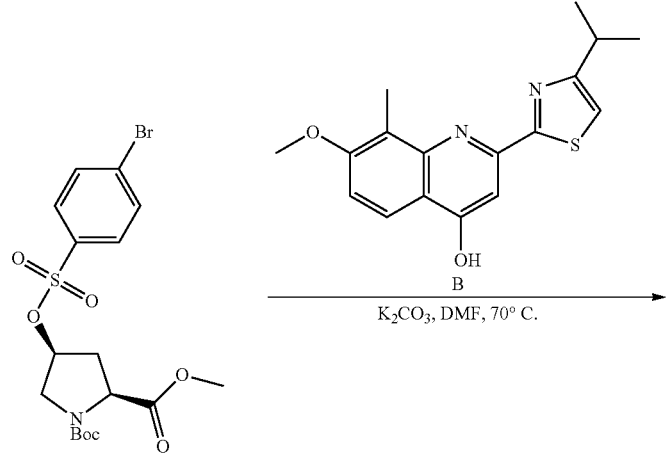

24

-continued
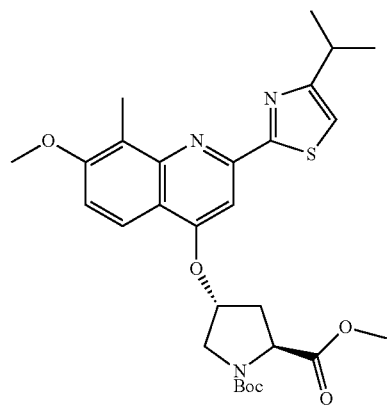
25
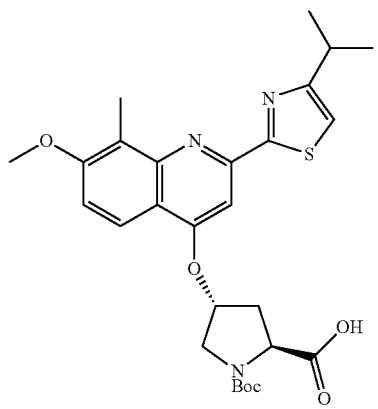
26
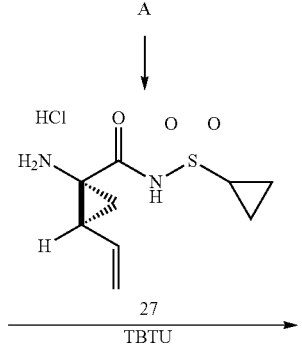
27
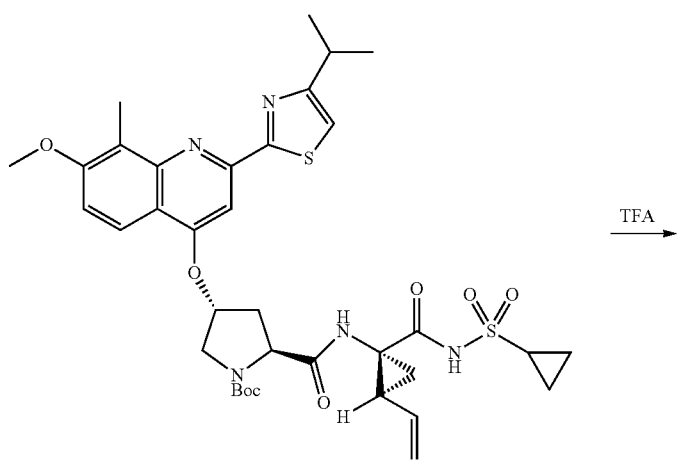
28
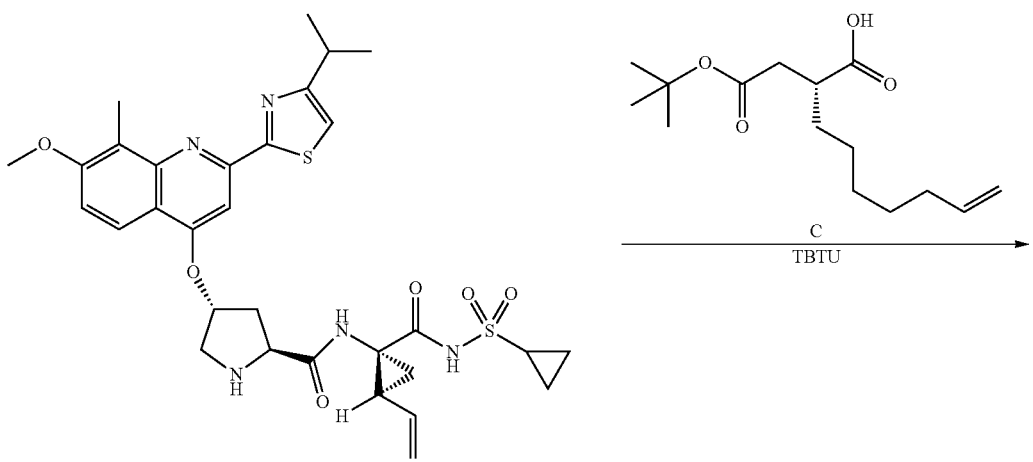
29

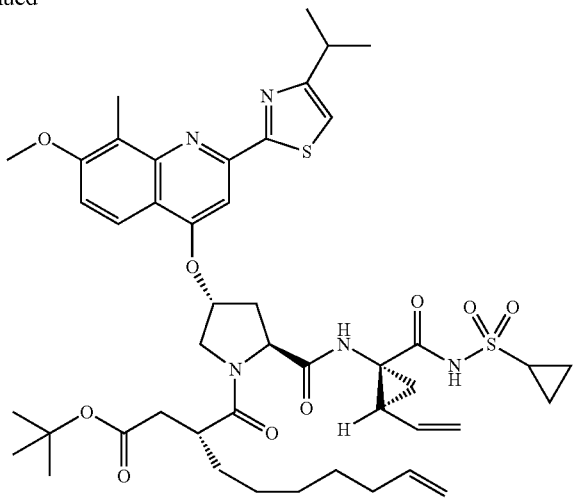

30

In particular, a lactone Compound 22 can be reacted in the presence of an acid catalyst such as Amberlyst-15 in methanol for a suitable time and temperature to obtain cis-hydroxy proline methyl ester (Compound 23) in high yield and then worked up to high purity.

A solution of the cis-hydroxyproline methyl ester (Compound 23) can then be reacted with triethylamine and catalytic dimethylaminopyridine in solvent and then reacted with Bromobenzene sulfonyl chloride (methanesulfonyl chloride can also be used) to obtain the brosylate (Compound 24), which can be used for the next step.

A solution of the brosylate (Compound 24) and Intermediate Compound B can be reacted with potassium carbonate or the like to obtain Compound 25.

Compound 25 can be reacted with aqueous lithium hydroxide or the like to obtain Compound 26.

Compound 27 can be obtained by treating Intermediate Compound A with acid to remove the Boc protecting group. Then Compound 27 can be reacted with Compound 26 in presence of TBTU (N,N,N',N'-Tetramethyl-O-(benzotriazol-1-yl)uronium tetrafluoroborate) or other coupling agents to obtain Compound 28. Other possible coupling agents may include benzotriazoles such as 1-[Bis(dimethylamino)methylene]-1H-1,2,3-triazolo[4,5-b]pyridinium 3-oxid hexafluorophosphate (HATU) or benzotriazol-1-yl-oxytripyrrolidinophosphonium hexafluorophosphate (PyBOP), carbodiimides such as N,N'-Dicyclohexylcarbodiimide (DCC) or 1-Ethyl-3-(3-dimethylaminopropyl)carbodiimide (EDC), or pyridinium salts such as 2-Chloro-1-methylpyridinium iodide (Mukaiyama's reagent).

A solution of Compound 28 in solvent can be reacted with trifluoroacetic acid (TFA) or other strong acids such as HCl to remove the Boc protecting group and obtain Compound 29. Compound 29 can be reacted with Intermediate Compound C in presence of TBTU or other coupling agents, including those mentioned for the synthesis of Compound 28. The reaction produces Compound 30.

Compound 30 can be used to prepare the product ACH-0142684.Na according to the following Reaction Scheme E.

Reaction Scheme E

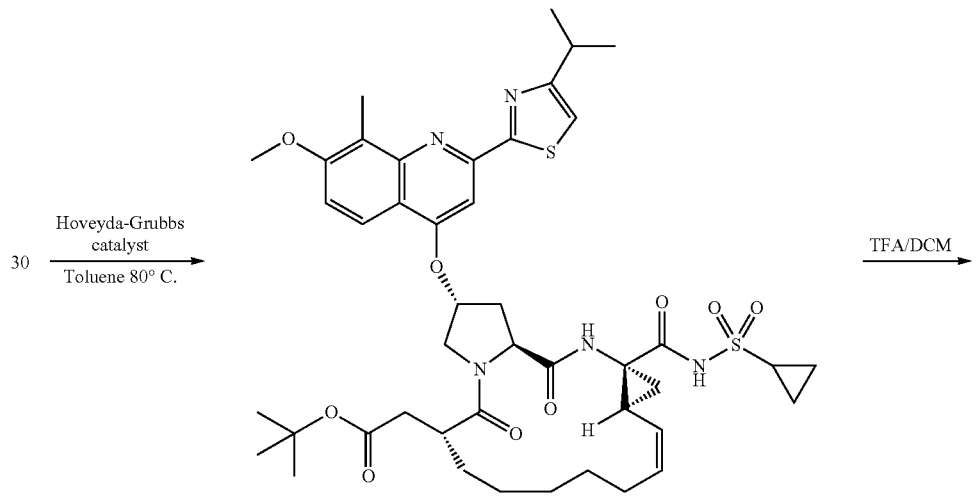

31

-continued
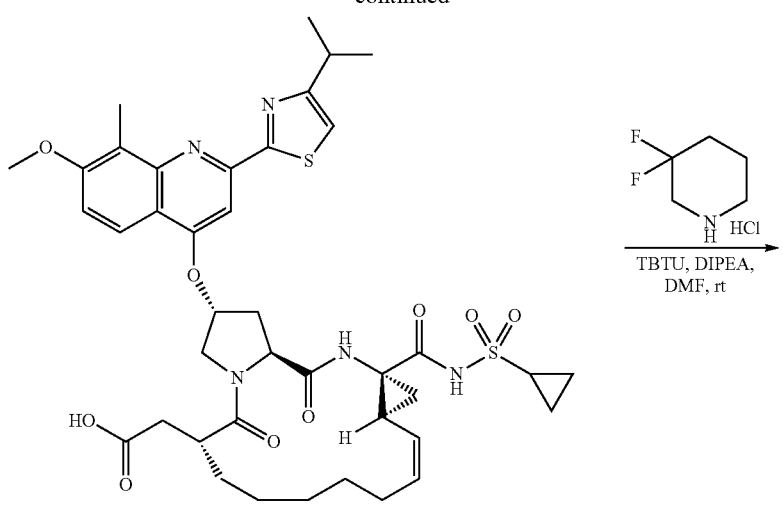
32
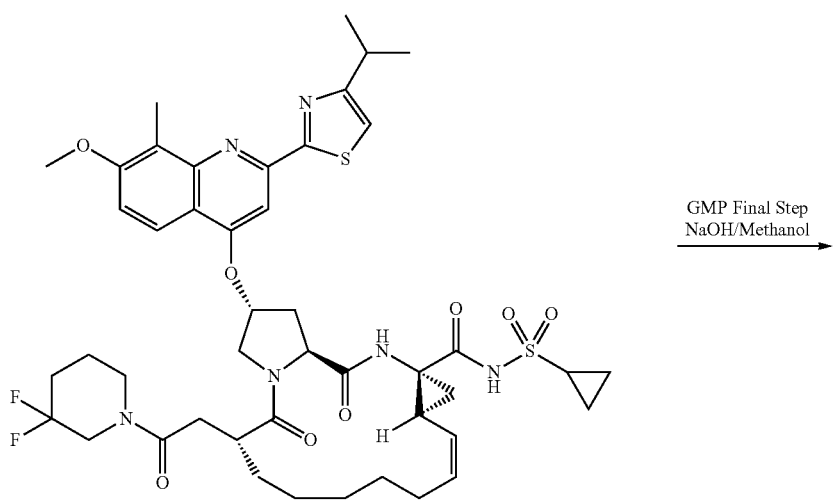
ACH-0142684
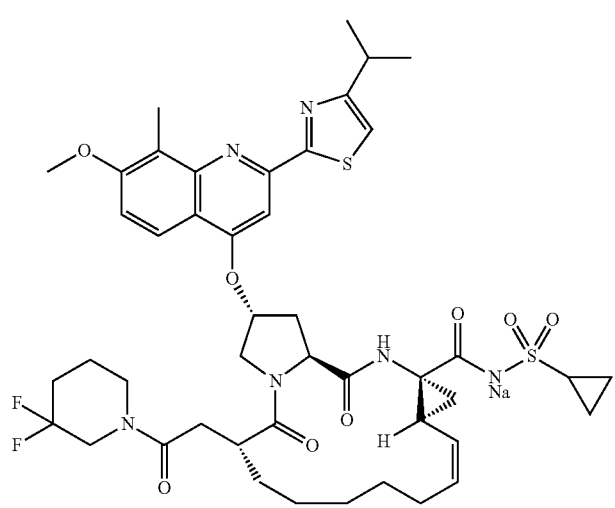
ACH-0142684.Na

Compound 31 can be obtained from Compound 30 using a cyclization catalyst such as the Hoveyda-Grubbs catalyst in toluene at 80-110° C. Alternatively Grubbs I catalyst, Grubbs II catalyst, or related analogs could be used. Heating can be continued until completion of the reaction.

Compound 31 can be treated with trifluoroacetic acid or other strong acid as in the synthesis of Compound 29 followed by diisopropylethylamine and 3,3-difluoropiperidine hydrochloride in a presence of a peptide coupling agent such as TBTU and a base such as diisopropyl ethylamine to give ACH-0142684. ACH-0142684 can be obtained in purified form by crystallization in suitable solvent such as isopropyl alcohol. Treatment with aqueous sodium hydroxide can provide the sodium salt (ACH-0142684.Na) thereof which can be obtained in crystalline form by crystallizing in a suitable solvent such as isopropyl alcohol, purification, and collection, as will be appreciated by one of ordinary skill in the art.

ACH-0142864 is a peptidomimetic compound comprised of amino acid like residues P1', P1, P2, P2-Top, P3, and P4. The presence of these residues in ACH-0142864 is shown in FIG. 1. The sequence of steps utilized to attach the amino acid residues can vary. The reaction schemes and Examples provide several reaction sequences by which amino acid residues P1', P1, P2, P2-Top, P3, and P4 can be attached to form ACH-0142864. However other sequences for attaching the amino acid residues to form ACH-0142864 are possible and will be readily apparent to those of skill in the art.

The disclosure includes the following embodiments.

The disclosure includes a process of preparing ACH-0142684, represented by the structure:

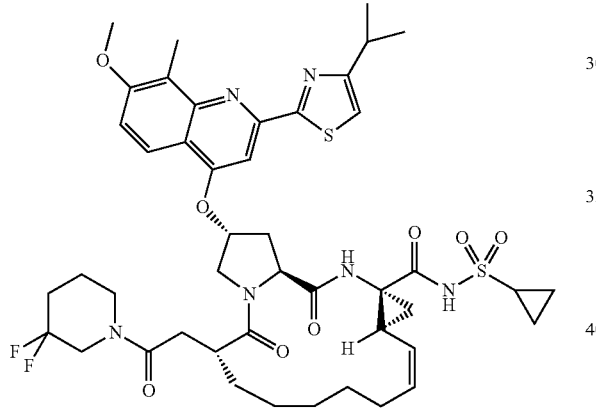

or its pharmaceutically acceptable salt from the intermediate compound represented by the structure:

(30)

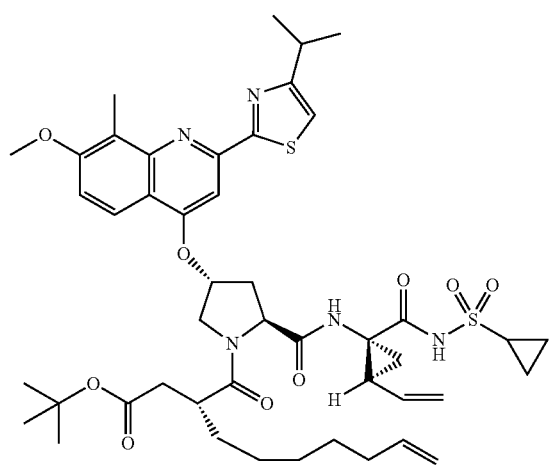

wherein the intermediate compound is reacted in the presence of a catalyst to join and merge the vinyl groups with the expulsion of ethylene, the butyl ester group is converted to a carboxylic acid group, and the carboxylic acid group is then reacted with 3,3-difluoropiperidine hydrochloride to provide ACH-0142684.

The catalyst used to join the ethylene groups may be a Grubbs I catalyst, a Grubbs II catalyst, or a Hoveyda-Grubbs catalyst or a combination of any of the foregoing.

The disclosure also includes a process of making a product intermediate compound (30),

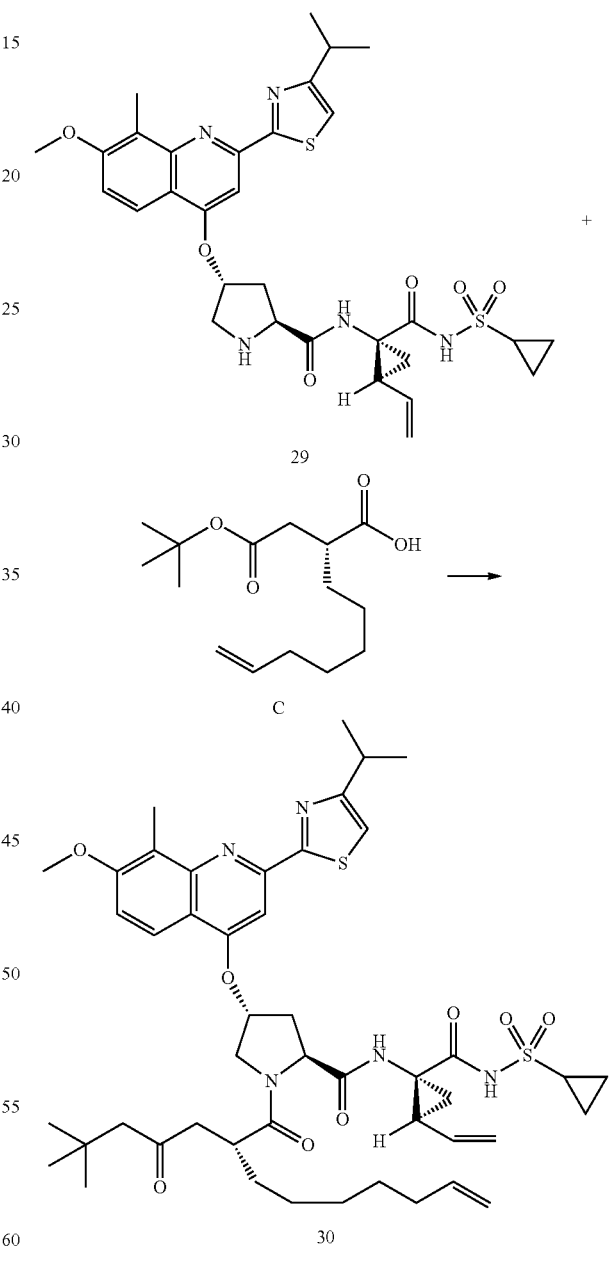

wherein an antecedent first intermediate compound (29) is reacted with an antecedent second intermediate Compound C to obtain the product intermediate compound (30).

The process for making the product intermediate (30) may additionally comprise obtaining the antecedent second intermediate Compound C by reacting nonenoic acid (19) with 4-benzyl-2-oxazolidinone to obtain an antecedent third intermediate compound (20)

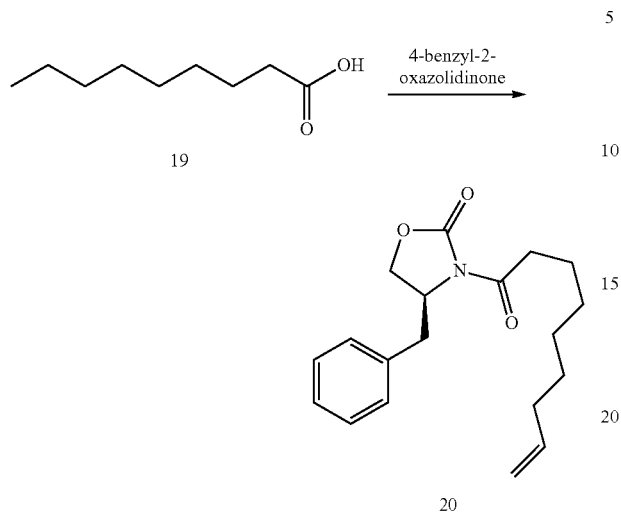

wherein the antecedent third intermediate compound (20) is then reacted with a strong base and t-butyl haloacetate to obtain an antecedent fourth intermediate compound (21), followed by reacting the antecedent fourth intermediate compound (21) with hydroxide peroxide in the presence of a base such as LiOH to provide Compound C.

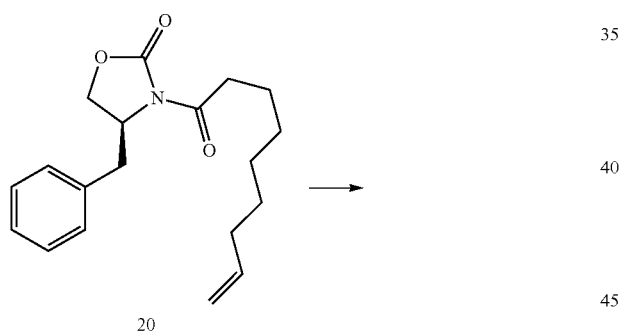

thereby obtaining the antecedent second intermediate compound C.

The strong base reacted with compound (20) and t-butyl halo acetate to obtain the antecedent fourth intermediate compound (21) may be sodium hexamethyldisilazide, potassium hexamethyldisilazide, lithium hexamethyldisilazide, lithium diisopropylamide, n-butyllithium, or a combination of any of the foregoing.

In certain embodiments the strong base is sodium hexamethyldisilazide.

The disclosure also includes a process for making the product intermediate (30) in which the nonenoic acid (19) is formed by reacting 1-bromo-hept-6-ene with an ethoxide salt and a dialkyl malonate in solvent.

The disclosure also includes a process for making the product intermediate (30) comprises reacting a compound (26), with (1R,2S)-1-amino-N-(cyclopropylsulfonyl)-2-vinylcyclopropanecarboxamide (27) in the presence of a peptide coupling agent to obtain a protected intermediate (28)

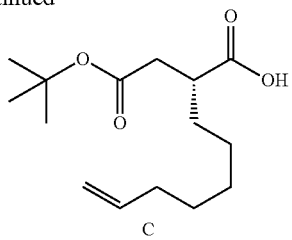

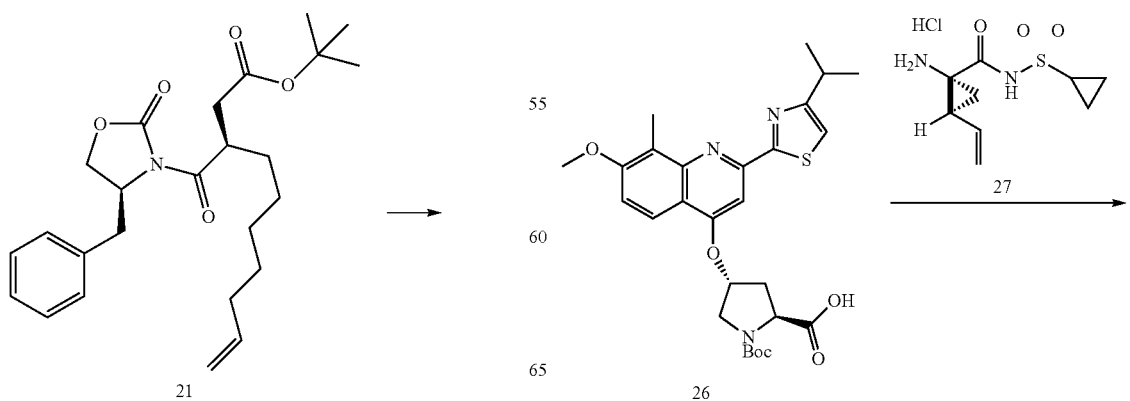

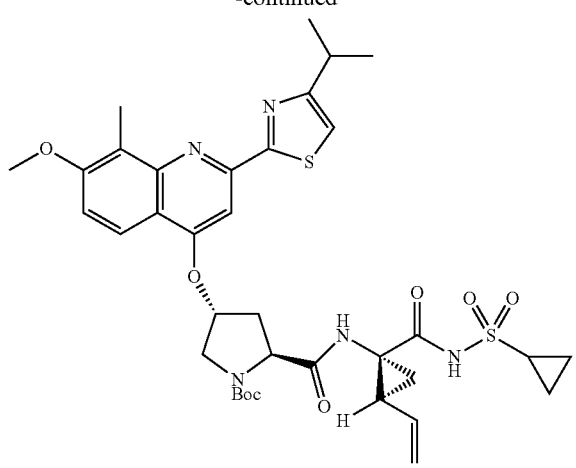

28 followed by deprotecting the protected intermediate (28) to obtain the first antecedent intermediate (29)

28

29

In this process the peptide coupling agent may be TBTU.

In this process the protected intermediate may be deprotected by reaction with a strong acid.

The disclosure includes a process of preparing a compound ACH-0142684 represented by the structure:

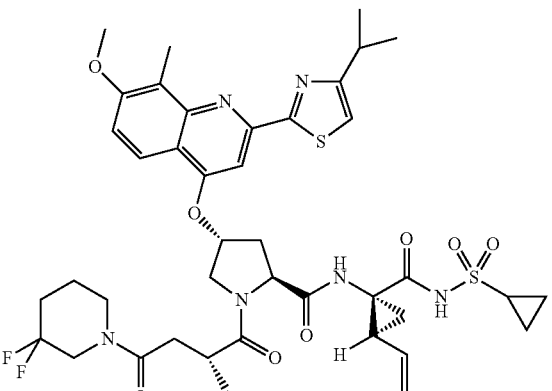

or its pharmaceutically acceptable salt, comprising reacting nonenoic acid (19) with 4-benzyl-2-oxazolidinone to obtain a compound (20);

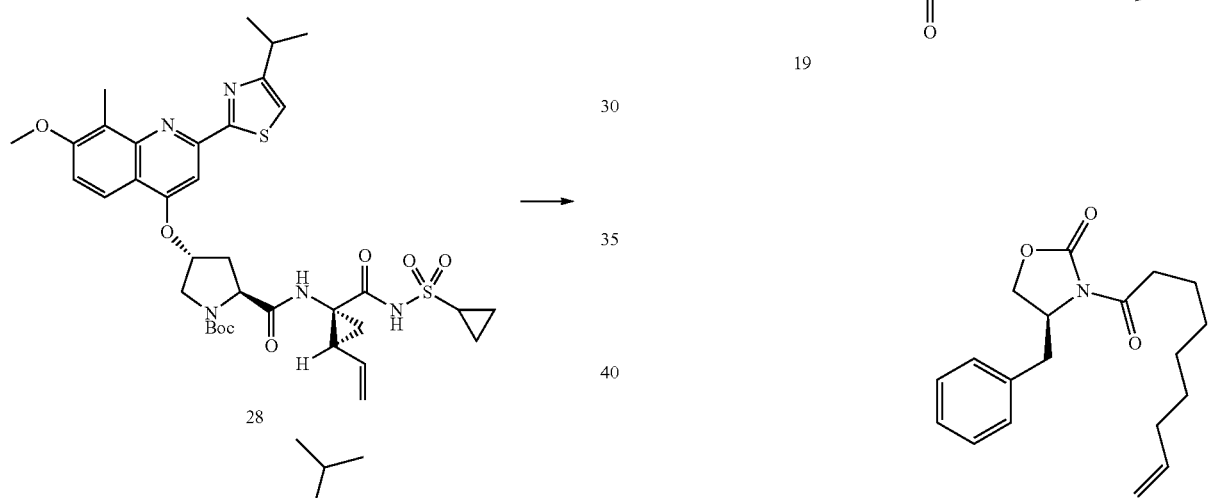

wherein the compound (20) is then reacted a strong base and t-butyl haloacetate to obtain a compound (21); followed by reacting the compound (21) with hydroxide peroxide in the presence of a base such as LiOH to provide Compound C;

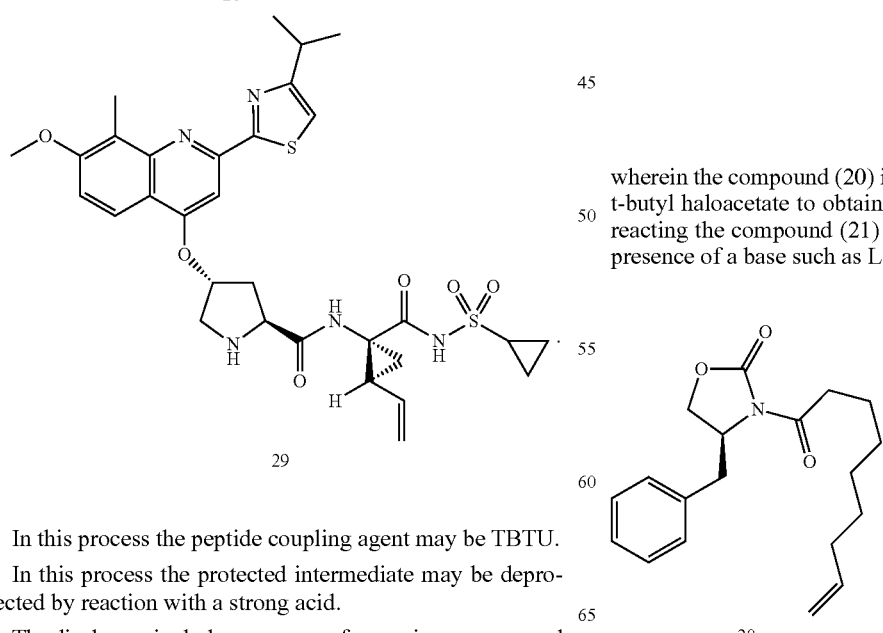

20

23
-continued

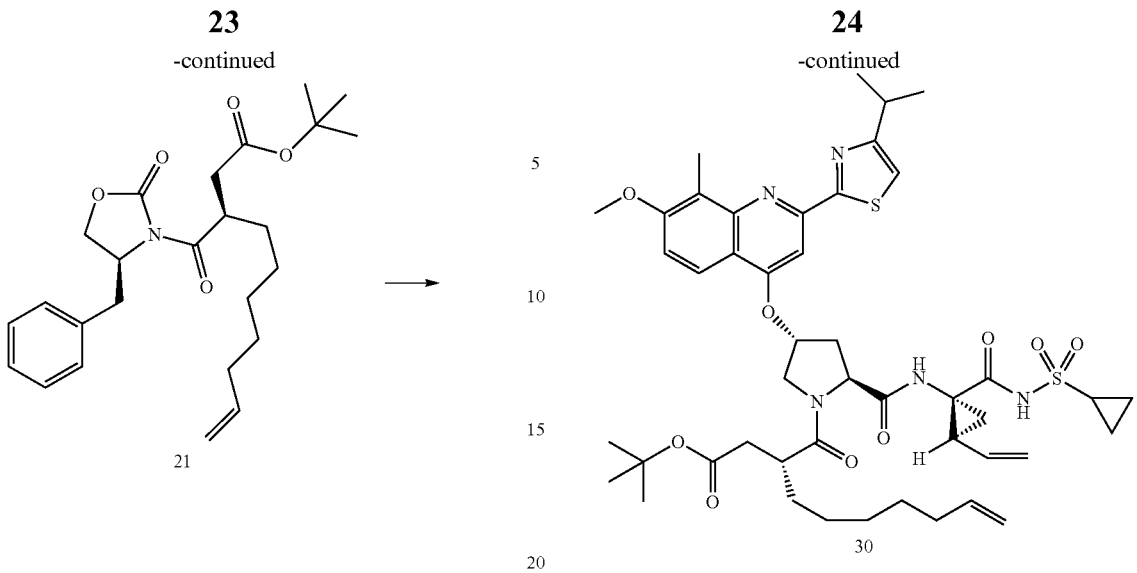

and reacting a compound (29) with the Compound C to obtain a compound (30);

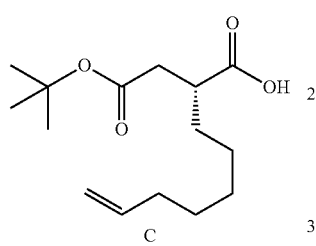

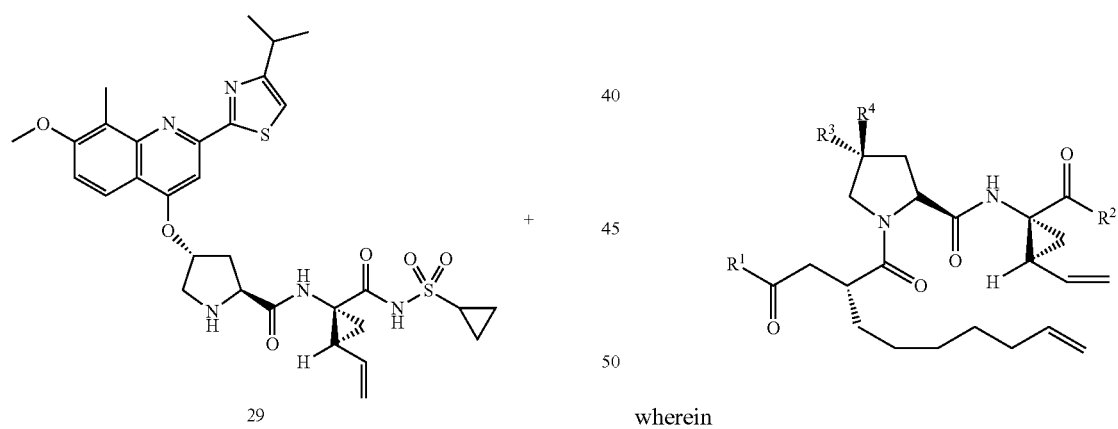

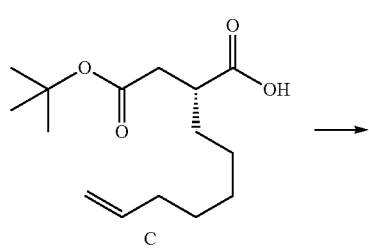

24
-continued wherein the compound (30) is reacted in the presence of a catalyst to join and merge the vinyl groups with the expulsion of ethylene, the butyl ester group is converted to a carboxylic acid group; and the carboxylic acid group is reacted with a salt of 3,3-difluoropiperidine;

thereby forming the compound ACH-0142684.

The disclosure includes an intermediate compound of the formula:

wherein $R^1$ is hydroxyl, $C_1$-$C_6$ alkoxy, aryloxy, benzyloxy, 4-methoxybenzyloxy, $C_1$-$C_6$ acyloxy, halogen, or N-linked 3,3-difluoropiperidinyl;

$R^2$ is hydroxyl, N-linked cyclopropylsulfonamide, or N-linked benzenesulfonamide in which the benzene ring is further substituted with 0-2 nitro groups; and $R^3$ is hydrogen and $R^4$ is halogen, hydroxyl, an O-linked mesylate group, or an O-linked benzenesulfonate group in which the benzene ring is further substituted with 0-1 groups independently chosen from $C_1$-$C_6$ alkyl, $C_1$-$C_6$ alkoxy, halogen, and nitro.

Or, R4 is hydrogen and R3 is hydroxyl or the heterocyclic group

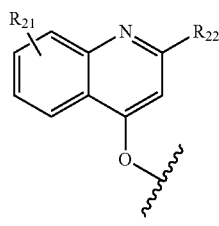

$R_{21}$, in this group, is 1 to 3 substituents independently chosen from halogen, hydroxyl, amino, cyano, —CONH$_2$, —COOH, $C_1$-$C_4$alkyl, $C_2$-$C_4$alkanoyl, $C_1$-$C_4$alkoxy, mono- and di-$C_1$-$C_4$alkylamino, $C_1$-$C_2$haloalkyl, and $C_1$-$C_2$haloalkoxy; and $R_{22}$ is phenyl, pyridyl, or thiazolyl, each of which is substituted with 0, 1, or 2 substituents independently chosen from halogen, hydroxyl, amino, cyano, —COOH, —CONH$_2$, $C_1$-$C_4$alkyl, $C_1$-$C_4$alkoxy, mono- and di-$C_1$-$C_4$alkylamino, trifluoromethyl, and trifluoromethoxy.

In certain embodiments the heterocyclic group is

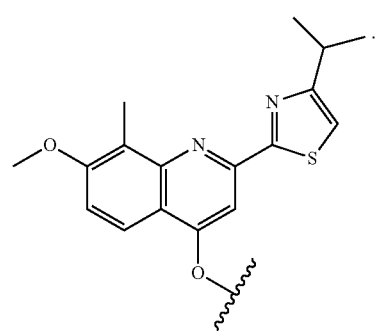 [SMILES: *Oc1cc(-c2nc(C(C)C)cs2)nc2c(C)c(OC)ccc12]

The disclosure includes an intermediate compound (30), having the following structure:

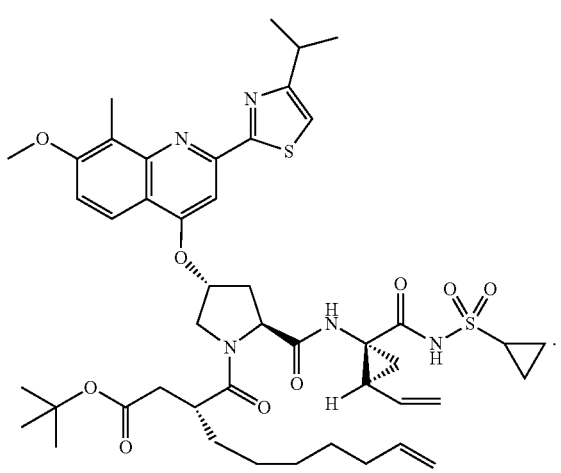

The disclosure includes a process for producing nonenoic acid, comprising Adding 1-bromo-hep-6-ene (18) to a malonate diester in a solvent to form a Compound (18-1)

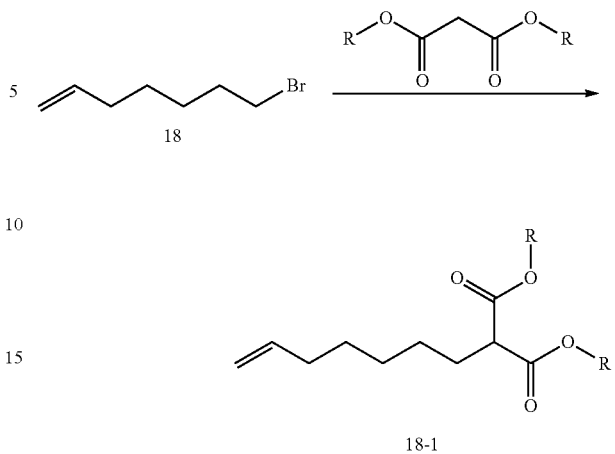

where each R is a $C_1$-$C_4$alkyl group; and eecarboxylation of the Compound (18-1) to provide nonenoic acid (19)

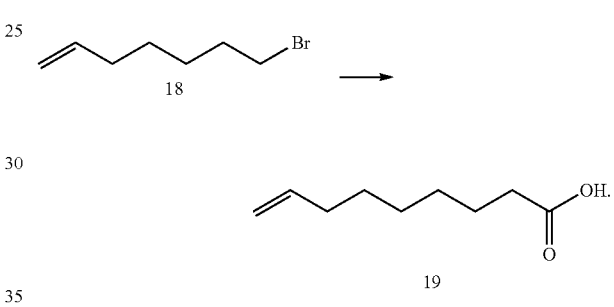

In an embodiment the malonate diester used to convert (18) to (18-1) is diethyl malonate (R is ethyl), ethoxide salt is added to the malonate diester, and the solvent is ethanol. In another embodiment R is ethyl, a strong base is added to the malonate diester is diethyl malonate (R is ethyl) and the solvent is an aprotic solvent, such as THF or DMF.

EXAMPLES

This invention is further illustrated by the following examples that should not be construed as limiting.

Example 1

Synthesis of Nonenoic Acid (Compound 19)

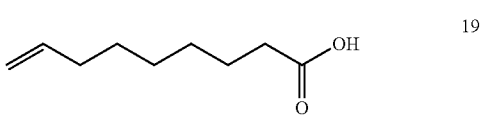

Sodium ethoxide was added to a solution of diethylmalonate in ethanol. To this solution was added 1-bromo-hept-6-ene. The reaction mixture was concentrated and then treated with aqueous potassium hydroxide. The reaction mixture was acidified and then heated at 140° C. to ensure decarboxylation and give nonenoic acid (19).

Example 2

Synthesis of Compound 30

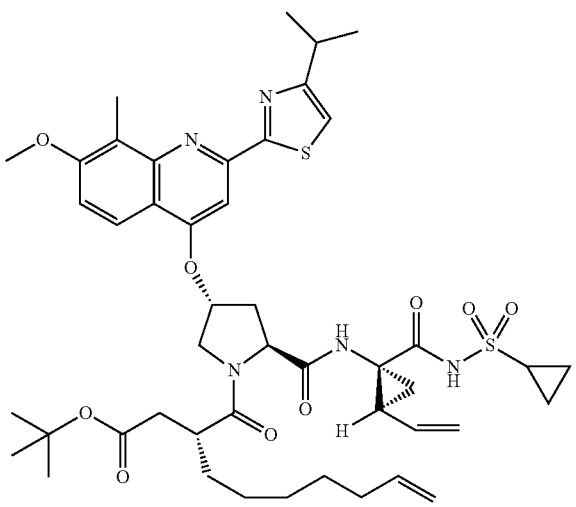

In accordance with Reaction Scheme D described above, the lactone (Compound 22, 1 equivalent) was stirred in methanol in the presence of Amberlyst-15® cation exchange resin (30% w/w) ( ) at room temperature for 18 hours. The resin was filtered and the filtrate evaporated to dryness to obtain cis-hydroxy proline methyl ester (Compound 23) having a purity of greater than 97%.

A solution of cis-hydroxyproline methyl ester (Compound 23, 1 equivalent), triethylamine and catalytic dimethylaminopyridine in dichloromethane was cooled to about 5° C. Methane sulfonyl chloride (1.5 equivalents), was added and stirred for 4 h. The solution was washed with 1M citric acid, water and brine. The organic layer was concentrated to obtain the brosylate (Compound 24) and used for the next step without any purification.

To a solution of the brosylate compound (Compound 24, 1 equivalent) and hydroxyquinoline (Intermediate Compound B, 0.95 equivalents) in DMF (dimethyl formamide) solvent is added potassium carbonate (1.3 equivalents) at room temperature. The reaction was stirred at 70° C. until the reaction was complete (about 18 hours) and added to 1M citric acid with vigorous stirring. The solid was isolated by filtration and dissolved in dichloromethane containing 5% methanol and filtered. The filtrate was concentrated and purified by chromatography over silica gel to give Compound 25 (purity>98%).

Compound 25 (1 equivalent) was dissolved in tetrahydrofuran and a solution of aqueous lithium hydroxide (1.5 equivalents) added at about 5° C. The reaction was stirred at room temperature until complete, about 3 h. The reaction mixture was concentrated and the residue slowly added to 1M citric acid with vigorous stirring. The solid precipitated was filtered and dried. The residue obtained was heated in heptane, cooled and filtered to obtain the acid (Compound 26, purity>97%). This solid was used in the next step without further purification.

To a cold (about 5° C.) solution of 4.5 N HCl in 1,4-dioxane was added Intermediate Compound A (1.5 equivalents relative to compound 26) and then stirred at room temperature until reaction was complete (about 3 hours). The reaction mixture was concentrated and the residue, Compound 27, was dissolved in dimethylformamide. To this solution was added the acid (Compound 26, 1 equivalent) and diisopropylethyl amine (1.5 equivalent) followed by TBTU (1.3 equivalents) at 5° C. The reaction mixture was stirred at room temperature until completion (about 18 hours). The reaction mixture was then added to a solution of 1M citric acid with vigorous stirring. The solid precipitated was isolated by filtration, dissolved in dichloromethane/5%-methanol, dried and concentrated. The residue obtained was heated in heptane, cooled and filtered to give Compound 28 (purity>96%).

A solution of compound 28 (1 equivalent) in dichloromethane was cooled to 5° C. and trifluoroacetic acid (TFA, 2.0 w/v) was added slowly. The reaction mixture was stirred at room temperature until complete, about 4 hours. All the volatiles were evaporated, residue dissolved in dichloromethane and evaporated again and the residue was dissolved in dimethylformamide. This solution was cooled to 5° C., diisopropypethyl amine (10 equivalents) and Compound C (1.4 equivalent) were added followed by TBTU (1.3 equivalents). The reaction mixture was stirred at room temperature until completion, about 18 hours. The reaction mixture was added to 1M citric acid and the solid isolate by filtration. The solid was dissolved in dichloromethane/5%-methanol washed with brine, dried and evaporated to dryness. The residue purified over silica gel and then crystallized from isopropyl alcohol to give Compound 30 (purity>98%).

Example 3

Synthesis of Sodium Salt of ACH-0142684

The synthesis of Sodium Salt of 2R,6R,14aR,16aS,Z)-N-(cyclopropylsulfonyl)-6-(2-(3,3-difluoropiperidin-1-yl)-2-oxoethyl)-2-(2-(4-isopropylthiazol-2-yl)-7-methoxy-8-methylquinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide:

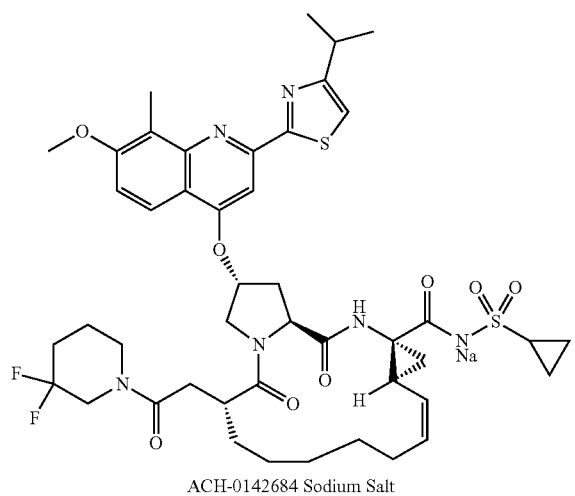

ACH-0142684 Sodium Salt

In accordance with Reaction Scheme E described above, Compound 30 (1 equivalent) was dissolved in toluene (1:56 w/v) and the solution degassed by bubbling nitrogen for 15 minutes. The reaction temperature was raised to 80-110° C. and Hoveyda-Grubbs catalyst (1-2 mol %) as a solution in toluene was added. Heating was continued until completion of the reaction and cooled to room temperature. Toluene was evaporated and the residue was purified by chromatography over silica gel. Solvent was evaporated from pooled fractions and the residue stirred with heptane and the solid filtered to obtain compound 31 (purity>98%).

Compound 31 (1 equivalent) was dissolved in dichloromethane, cooled to 5° C. and trifluoroacetic acid (2-3 w/v) was added and stirred at room temperature for 4 h. The reaction mixture was concentrated and the residue dissolved in dimethylformamide and cooled to 5° C. before addition of diisopropylethyl amine (10 equivalents). TBTU (1.8 equivalents) was added followed by 3,3-difluoropiperidine hydrochloride (1.2 equivalents). The reaction was stirred until completion and added to 1M citric acid and solid collected by filtration. The solid was crystallized from ethylacetate/heptane to give ACH-0142684 (1 purity>98%). ACH-0142684 was suspended in methanol and aqueous sodium hydroxide (1.05 equivalents) was added at about 5° C. to give a clear solution. The reaction mixture was concentrated to dryness and the residue crystallized from IPA to give crystalline ACH-0142684·Na. The crystalline ACH-0142684.Na was dissolved in a mixture of methanol/ethyl acetate and the solution was added to pentane. The solid was collected by filtration and dried to give ACH-0142684·Na in the amorphous form (purity>98%).

Starting materials are generally readily available from commercial sources, such as Sigma-Aldrich Corp. (St. Louis, Mo.). It will be apparent that the final product and any intermediate(s) shown in the following schemes may be extracted, dried, filtered and/or concentrated, and may be further purified (e.g., by chromatography). Reaction Schemes, refers to any group consistent with the description of the compounds provided herein. An individual skilled in the art may find modifications of one or several of the synthetic steps described herein without diverting significantly from the overall synthetic scheme.

What is claimed is:

1. A process of preparing a compound, ACH-0142684, represented by the structure:

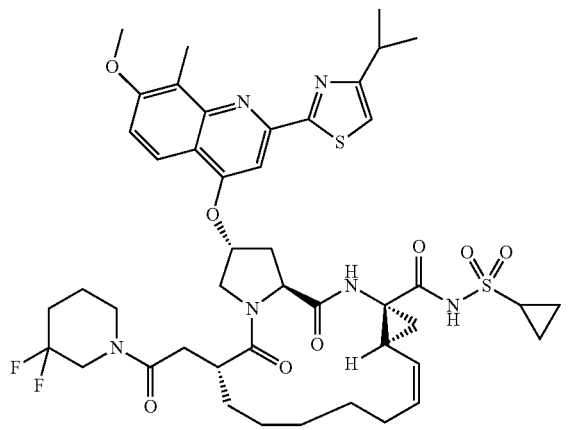 [SMILES: COc1ccc2c(O[C@@H]3C[C@H]4C(=O)N[C@]5(C(=O)NS(=O)(=O)C6CC6)C[C@H]5/C=C\CCCCC[C@H](CC(=O)N5CCCC(F)(F)C5)C(=O)N4C3)cc(-c3nc(C(C)C)cs3)nc2c1C]

or its pharmaceutically acceptable salt from an intermediate compound represented by the structure:

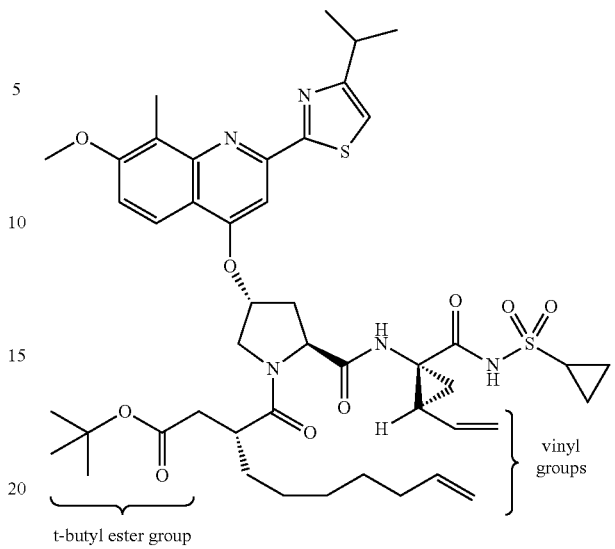

wherein the intermediate compound is reacted in the presence of a catalyst to join and merge the vinyl groups with the expulsion of ethylene, the t-butyl ester group is converted to a carboxylic acid group, and the carboxylic acid group is then reacted with 3,3-difluoropiperidine to provide ACH-0142684.

2. The process of claim 1 wherein the catalyst to join the ethylene groups is a Grubbs I catalyst, a Grubbs II catalyst, or a Hoveyda-Grubbs catalyst or a combination of any of the foregoing.

3. A process of making a product intermediate compound (30),

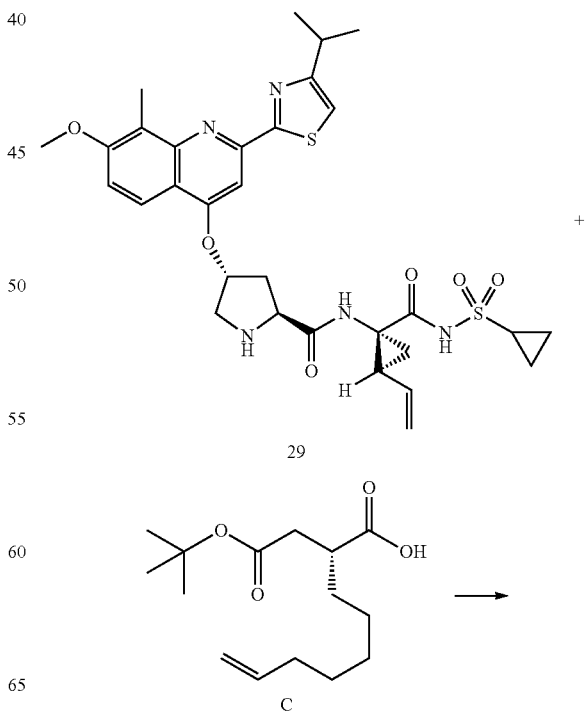

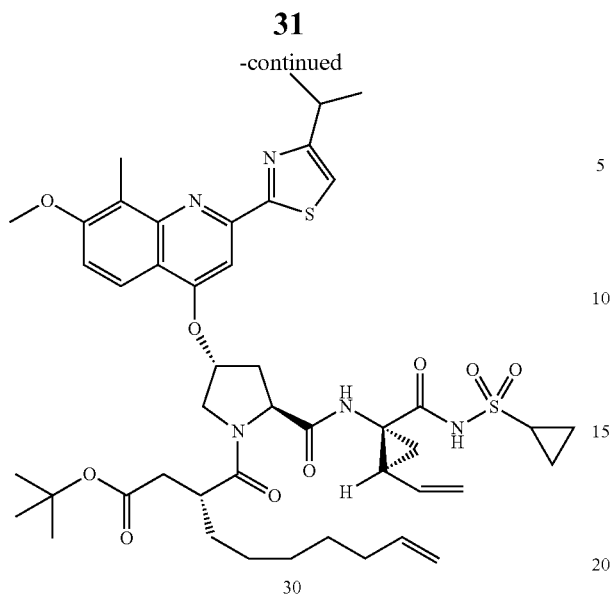

30 wherein an antecedent first intermediate compound (29) is reacted with an antecedent second intermediate Compound C to obtain the product intermediate compound (30).

4. The process of claim 3 additionally comprising obtaining the antecedent second intermediate Compound C by reacting nonenoic acid (19) with 4-benzyl-2-oxazolidinone to obtain an antecedent third intermediate compound (20)

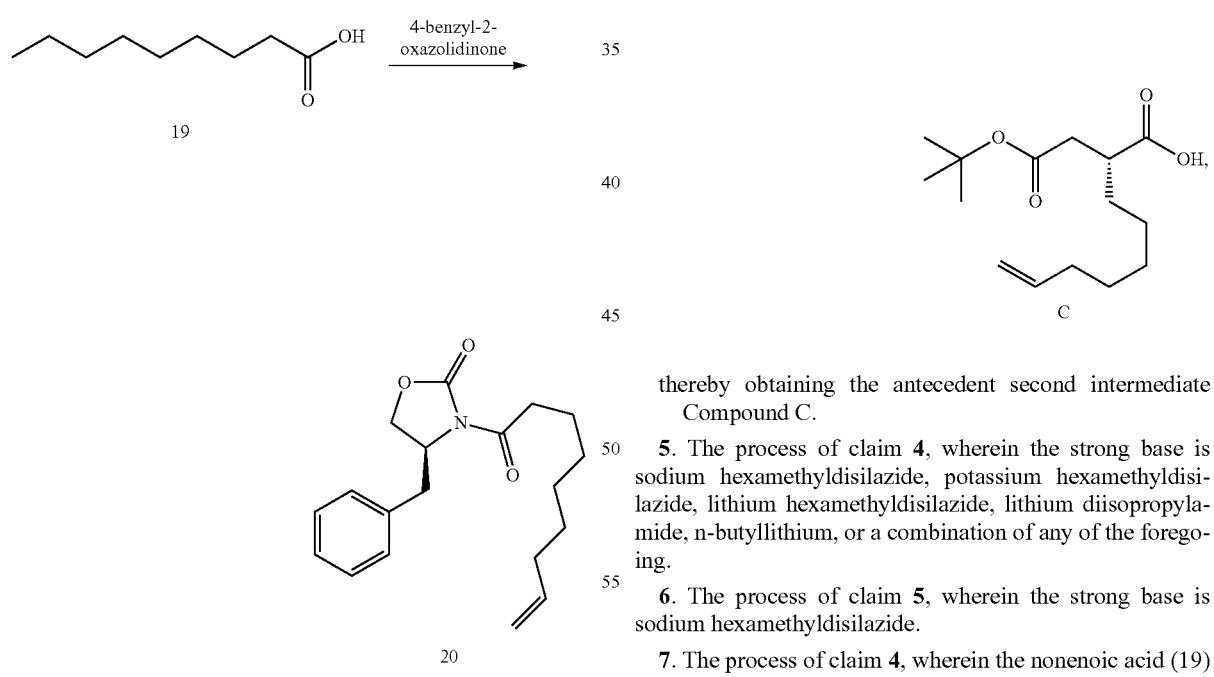

wherein the antecedent third intermediate compound (20) is then reacted with a strong base and t-butyl haloacetate to obtain an antecedent fourth intermediate compound (21);

followed by reacting the antecedent fourth intermediate compound (21) with hydroxide peroxide in the presence of a base such as LiOH to provide Compound C, thereby obtaining the antecedent second intermediate Compound C.

5. The process of claim 4, wherein the strong base is sodium hexamethyldisilazide, potassium hexamethyldisilazide, lithium hexamethyldisilazide, lithium diisopropylamide, n-butyllithium, or a combination of any of the foregoing.

6. The process of claim 5, wherein the strong base is sodium hexamethyldisilazide.

7. The process of claim 4, wherein the nonenoic acid (19) is formed by reacting 1-bromo-hept-6-ene with an ethoxide salt and a dialkyl malonate in solvent.

8. The process of claim 3, where the process further comprises reacting a compound (26),
with (1R,2S)-1-amino-N-(cyclopropylsulfonyl)-2-vinyl-cyclopropanecarboxamide (27) in the presence of a peptide coupling agent to obtain a protected intermediate (28)

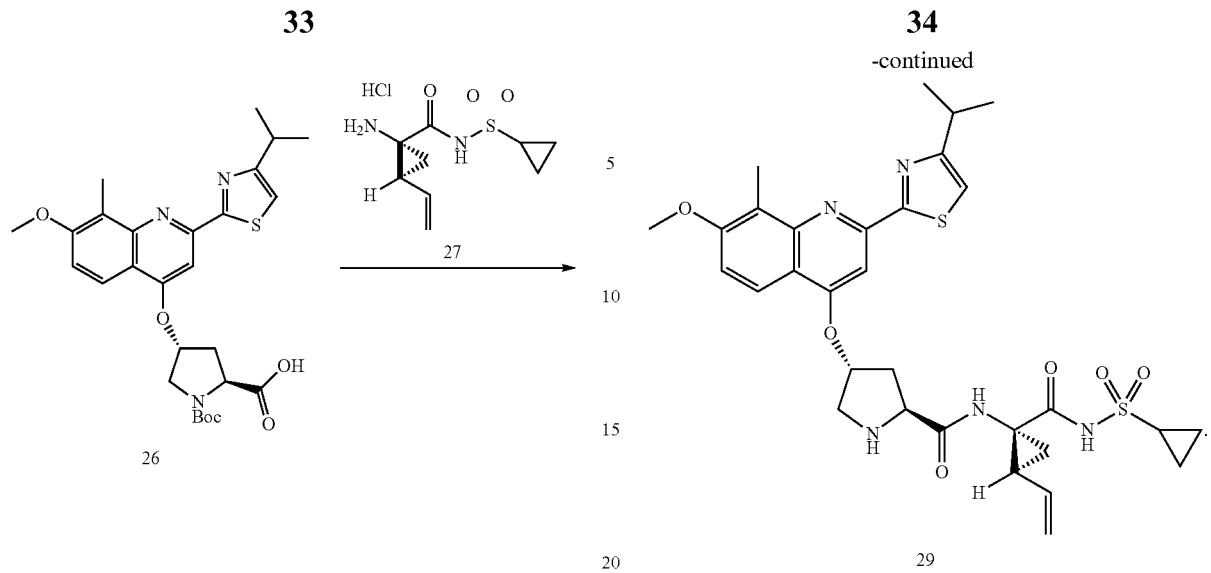

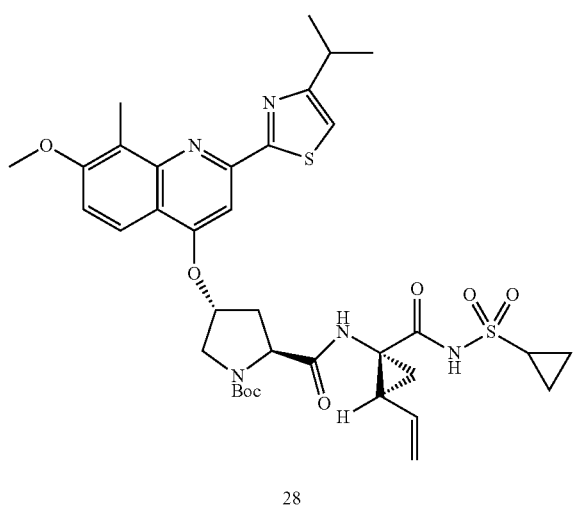

followed by deprotecting the protected intermediate (28) to obtain the first antecedent intermediate (29)

9. The process of claim 8, wherein the peptide coupling agent is N,N,N',N'-tetramethyl-O-(benzotriazol-1-yl)uronium tetrafluoroborate (TBTU), [Bis(dimethylamino)methylene]-1H-1,2,3-triazolo [4,5-b]pyridinium 3-oxid hexafluorophosphate (HATU), benzotriazol-1-yl-oxytripyrrolidinophosphonium hexafluorophosphate (PyBOP), N,N'-Dieyclohexylcarbodiimide (DCC), 1-Ethyl-3-(3-dimethylamininopropyl)carbodiimide (EDC), 2-Chloro-1-methylpyridinium iodide (Mukaiyama's reagent), or a combination of any of the foregoing.

10. The process of claim 9, wherein the peptide coupling agent is N,N,N',N'-tetramethyl-O-(benzotriazol-1-yl)uronium tetrafluoroborate (TBTU).

11. The process of claim 10, wherein the protected intermediate is deprotected by reaction with a strong acid.

12. A process of preparing a compound, ACH-0142684, represented by the structure:

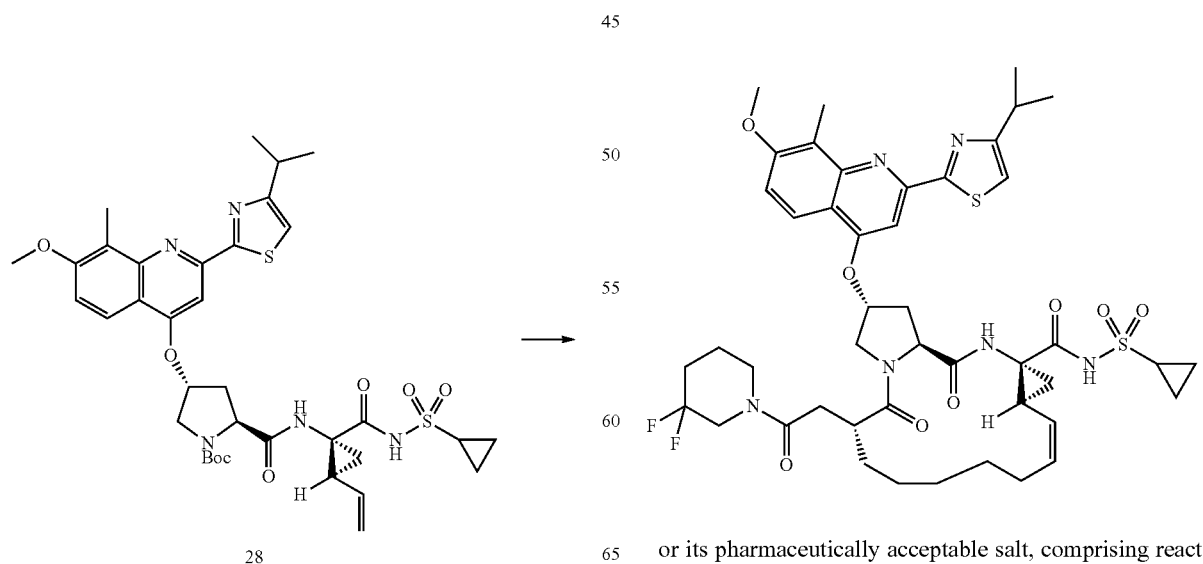

or its pharmaceutically acceptable salt, comprising reacting nonenoic acid (19) with 4-benzyl-2-oxazolidinone to obtain a compound (20);

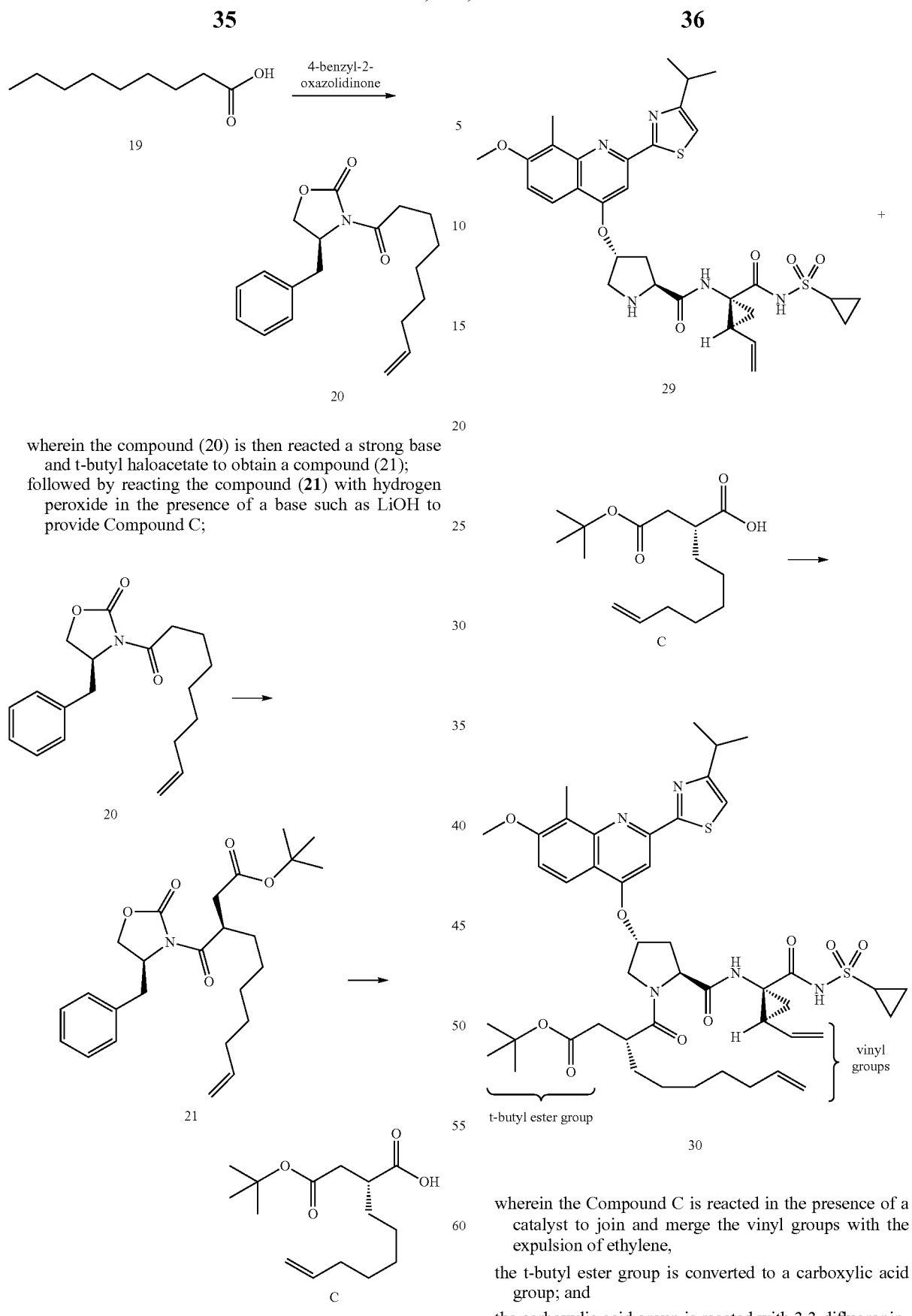

wherein the compound (20) is then reacted a strong base and t-butyl haloacetate to obtain a compound (21);
followed by reacting the compound (21) with hydrogen peroxide in the presence of a base such as LiOH to provide Compound C;

reacting a compound (29) with the Compound C to obtain a compound (30)

wherein the Compound C is reacted in the presence of a catalyst to join and merge the vinyl groups with the expulsion of ethylene, the t-butyl ester group is converted to a carboxylic acid group; and the carboxylic acid group is reacted with 3,3-difluoropiperidine;

thereby forming the compound ACH-0142684.

13. An intermediate compound of the formula:

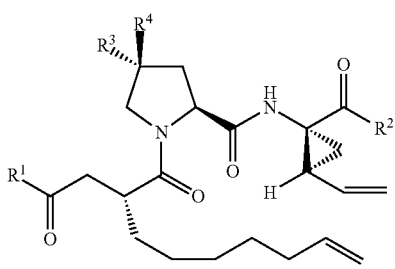

wherein
- $R^1$ is hydroxyl, $C_1$-$C_6$ alkoxy, aryloxy, benzyloxy, 4-methoxybenzyloxy, $C_1$-$C_6$ acyloxy, halogen, or N-linked 3,3-difluoropiperidinyl;
- $R^2$ is hydroxyl, N-linked cyclopropylsulfonamide, or N-linked benzenesulfonamide in which the benzene ring is further substituted with 0-2 nitro groups; and
- $R^4$ is hydrogen and $R^3$ is hydroxyl or the heterocyclic group

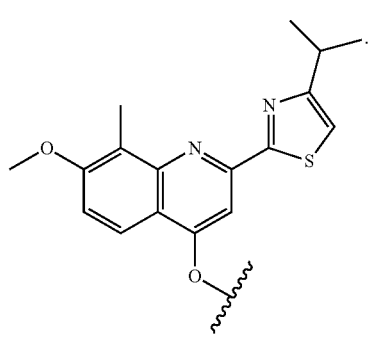 [SMILES: *Oc1cc(-c2nc(C(C)C)cs2)nc2c(C)c(OC)ccc12]

$R_{21}$, in this group, is 1 to 3 substituents independently chosen from halogen, hydroxyl, amino, cyano, —$CONH_2$, —COOH, $C_1$-$C_4$alkyl, $C_2$-$C_4$alkanoyl, $C_1$-$C_4$alkoxy, mono- and di-$C_1$-$C_4$alkylamino, $C_1$-$C_2$haloalkyl, and $C_1$-$C_2$haloalkoxy; and $R_{22}$ is phenyl, pyridyl, or thiazolyl, each of which is substituted with 0, 1, or 2 substituents independently chosen from halogen, hydroxyl, amino, cyano, —COOH, —$CONH_2$, $C_1$-$C_4$alkyl, $C_1$-$C_4$alkoxy, mono- and di-$C_1$-$C_4$alkylamino, trifluoromethyl, and trifluoromethoxy.

14. The intermediate compound of claim 13, having the following structure:

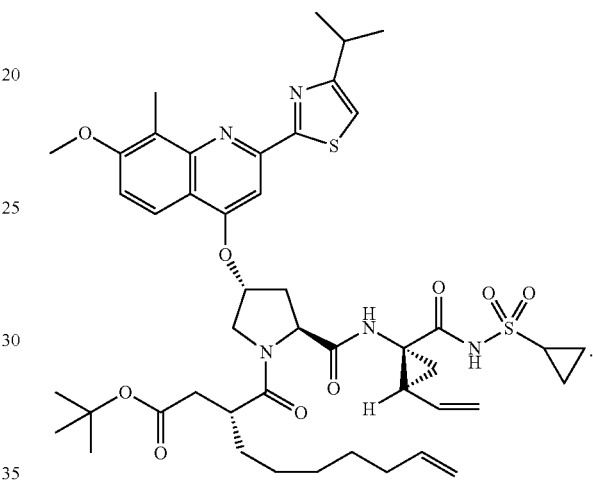

(30)

* * * * *